United States Patent [19]

Biot et al.

[11] 4,412,452

[45] Nov. 1, 1983

[54] HARMONIC OSCILLATOR FOR MEASURING DYNAMIC ELASTIC CONSTANTS OF ROCK MATERIALS

[75] Inventors: Maurice A. Biot, Brussels, Belgium; William L. Medlin; Lucien Masse', both of Dallas, Tex.

[73] Assignee: Mobil Oil Corporation, New York, N.Y.

[21] Appl. No.: 231,716

[22] Filed: Feb. 5, 1981

[51] Int. Cl.³ ............................................ G01N 29/00
[52] U.S. Cl. ....................................................... 73/579
[58] Field of Search ................. 73/579, 597, 574, 576, 73/578, 808, 573, 811

[56] References Cited

U.S. PATENT DOCUMENTS

| | | | |
|---|---|---|---|
| 1,414,077 | 4/1922 | Fessenden | 73/579 |
| 3,320,796 | 10/1963 | Darby | 73/576 |
| 3,489,161 | 1/1970 | Rexford | 73/579 |
| 4,058,007 | 11/1977 | Exner | 73/DIG. 1 |

OTHER PUBLICATIONS

"Effects of Pressure and Fluid Saturation on the Attenuation of Elastic Waves in Sands", by G. H. F. Gardner, et al.; *Journal of Petroleum Technology;* Feb. 1964; pp. 189-198, Petroleum Transactions.
"The Attenuation Constant of Earth Materials", by W. T. Born, pp. 132-147.
"A New Approach to the Study of Elastic Propagation in Rocks" by F. F. Evision.
"Internal Friction in Shear and Shear Modulus of Solenhofen Limestone Over a Frequency Range of $10^7$ Cycles per Second", by Louis Peselnick and W. F. Outerbridge; *Journal of Geophysical Research* vol. 66, No. 2, Feb. 1961.
"Propagation of Elastic Waves in a Cylindrical Bore Containing a Fluid", by M. A. Biot; *Journal of Applied Physics;* vol. 23, No. 9, Sep. 1952.
"Permeability Profiles From Acoustic Logging", by J. J. Staal; *Society of Petroleum Engineers of AIME*.
"The Variation of the Elastic Constants of Rocks with Frequency", by Dr. J. McG. Bruckshaw and P. C. Mahanta; Petroleum, Jan. 1954.
"A Review of the Progress in the Measurement of Dynamic Elastic Properties", by K. W. Hillier.
"Elastic Behaviour of Rocks at Low Frequencies", by M. J. Usher *Geophysical Prospecting X.*

*Primary Examiner*—Anthony V. Ciarlante
*Attorney, Agent, or Firm*—Charles A. Huggett; Michael G. Gilman; George W. Hager

[57] ABSTRACT

A simple harmonic oscillator for use in measuring dynamic elastic constants of rock material samples includes a pair of masses vertically suspended from a support position by a pair of wires. At least one mass is driven by a permanent magnet with the driving coil positioned in the air gap to the magnet. The rock sample is horizontally positioned between the pair of masses such that the rock sample acts as a spring element connecting the masses, thereby forming the simple harmonic oscillator.

8 Claims, 5 Drawing Figures

NORMALIZED DRIVING CURRENT I VS FREQUENCY IN A BEREA SAMPLE

HARMONIC OSCILLATOR FOR MEASURING DYNAMIC ELASTIC CONSTANTS OF ROCK MATERIALS

BACKGROUND OF THE INVENTION

Many seismic investigation techniques have been developed. For the most part these investigations have been guided by three main sources of data: field seismic records, well logs, and laboratory measurements of ultrasonic pulse velocities in core samples of rock materials. With respect to ultrasonic pulse velocity measurements the travel time of an ultrasonic wavelet is measured between ends of a cylindrical or prismatic bar of rock material. The wavelength of the ultrasonic signal must be small compared to the length of the bar so that the wavelet has time to die out at the excitation end before it is detected at the receiving end. For samples of practical length the signal frequency must be of the order of hundreds of kHz. Seismic data are limited to frequencies below a few hundred hertz. Consequently the ultrasonic pulse velocity technique has not permitted measurements at frequencies approaching the seismic range.

SUMMARY OF THE INVENTION

In accordance with the present invention, there is disclosed a new and improved system for measuring dynamic Young's modulus of rock materials in the seismic frequency range.

More particularly, a harmonic oscillator includes a pair of masses vertically suspended from a support position by a pair of thin wires. At least one of such masses is driven by a permanent magnet with driving coil positioned within its air gap. A sinusoidal frequency is applied to such coil for applying the drivinng force through the magnet to the mass. A rock material sample is positioned horizontally between the pair of masses and acts as the spring element of a simple spring-mass harmonic oscillator system.

In a further aspect, a pair of motion detectors is attached to each of the masses. These detectors consist of a pair of small permanent magnets with coils positioned within their air gaps. Motion of the masses produces an electrical signal in the coils. For sinusoidal motion of the masses the amplitude of the sine wave produced by the detectors is proportional to the velocity of the masses at any instant. The integral of this signal is a cosine wave whose amplitude is proportional to the displacement of the masses at any instant.

DESCRIPTION OF THE PREFERRED EMBODIMENT

The present invention relates to a system for measuring dynamic Young's modulus of rock material at seismic frequencies from which wave velocities and attenuation coefficients can be determined.

In accordance with the present invention, a resonance measurement technique is used in a harmonic oscillator system to determine the dynamic Young's modulus of a vibrating rock sample at seismic frequency. The dynamic Young's modulus determined in this way can be used to compute velocity from the equations of linear elasticity theory. This calculated velocity is, however, merely an approximation since rock materials do not behave like an ideal elastic material. To the extent that they do, the resonance method provides an indirect means of measuring velocity at seismic frequency. Velocities determined by this method can then be compared with those measured at logging and ultrasonic frequencies in the same rock material.

Figure 1:
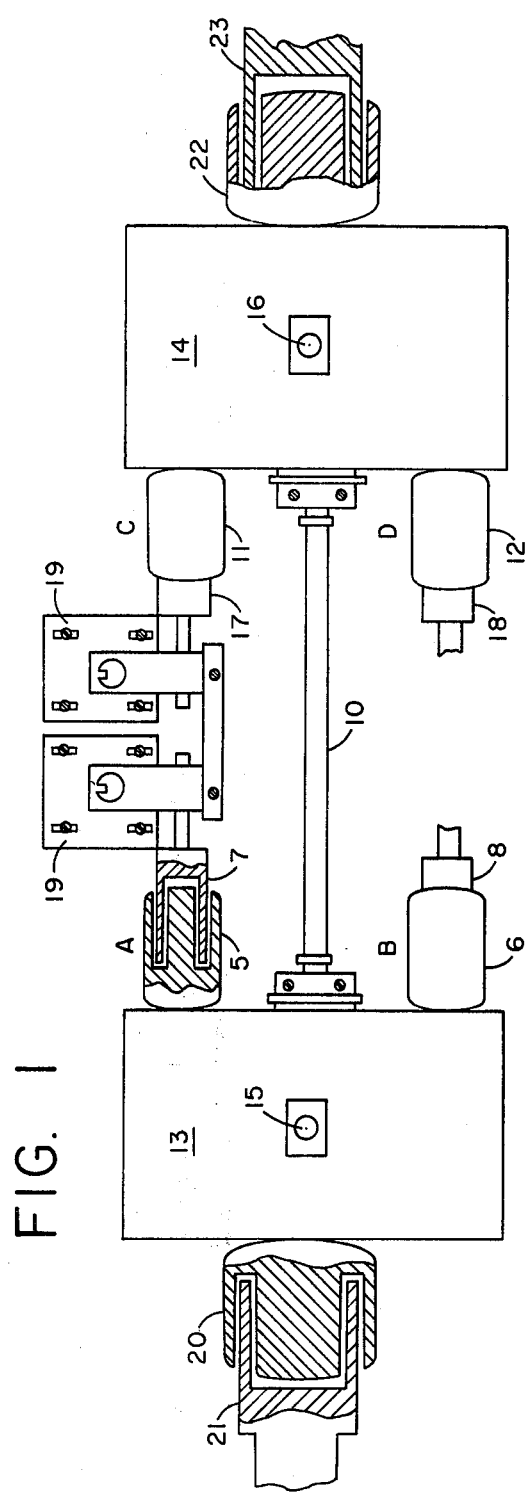
FIG. 1 illustrates the harmonic oscillator of the present invention.

In FIG. 1 there is illustrated the mechanical harmonic oscillator of the present invention. It utilizes the concept of a mass-spring system with a rock sample acting as the spring. The resonant frequency is determined not only by the dimensions of the rock, which control the spring constant, but by the mass, which can be made very large. By using a large enough mass, resonant frequencies in the seismic range are produced with rock samples of 6 to 10 inches in length. Thus, it is not necessary to make measurements far below the resonant frequency or to use samples of impractical dimensions.

Another feature of the invention relates to parasitic damping effects. The spring-mass system can keep such parasitic damping negligibly low. Since the dynamic properties of many rock materials, such as elastic constants and gross behavior as a function of frequency and saturation conditions are amplitude sensitive, it is important that the amplitude of oscillation be kept at or near seismic levels.

Referring now to FIG. 1, the rock sample 10 is bonded in a horizontal position between the two masses 13 and 14 which are suspended from a fixed support (not shown) by means of the wires 15 and 16 respectively. The support is seismically isolated from the earth. Mass 13 is attached to a permanent magnet 20 while mass 14 is attached to a permanent magnet 22. Driving coils 21 and 23 are positioned in the air gaps of the magnets 20 and 22, respectively to provide a conventional means for applying driving forces to the masses 13 and 14. A sinusoidal signal of frequency f is applied to each coil with the appropriate polarity to drive masses in opposition.

The system has two natural modes of vibration, a high frequency one in which the two masses, 13 and 14, move in opposite directions and a lower frequency one in which they move in the same direction. Longitudinal oscillations are produced in the rock sample 10 when the masses move in opposition. This condition is provided when the system is symmetrical, that is, when the masses 13 and 14 are equal, the lengths of wires 15 and 16 are equal, the driving currents to the coils 21 and 22 are equal, and the magnetic field strengths in the air gaps of the magnets are equal. Under such conditions, the low frequency mode is largely eliminated and there is a single prominent resonance. The resonant frequency with no damping, $f_o$, is given by $$f_o = \frac{1}{2\pi} \sqrt{\frac{g}{h} + \frac{2K}{M}} \quad (1)$$

where g is acceleration due to gravity, M is mass, h is wire length, and K is the spring constant of the rock. With damping, the resonant frequency, $f_m$, is given by $$f_m = f_o \sqrt{1 - 2\epsilon^2} \qquad (2)$$

where $\epsilon$ is a damping coefficient given by $\frac{1}{4}$ times the fractional energy loss per cycle of oscillation. In practice $g/h << 2 K/M$ and if damping is small, $2\epsilon^2 << 1$. Then $$f_m \approx \frac{1}{2\pi} \sqrt{\frac{2K}{M}} \qquad (3)$$

If the rock is treated as an elastic material, K is related to Young's modulus through the equation $$K = \frac{EA}{L} \qquad (4)$$

where A is cross-sectional area and L is length of the rock sample. The bar velocity V in a cylindrical core or prismatic bar of material with modulus E is given by $$V = \sqrt{E/\rho} = 2\pi f_m \sqrt{\frac{ML}{A\rho}} \qquad (5)$$

where $\rho$ is density of the material.

To the extent that a given rock material is perfectly elastic in behavior, and the system of FIG. 1 is free of damping, equation (5) can be used to determine a bar velocity from measurement of resonant frequency $f_m$. The bar velocity is the velocity a seismic wave would have in a thin prismatic bar such as the rock sample of FIG. 1. Velocity of a seismic wave in the earth is related to bar velocity as follows:

$$V_{earth} = V\sqrt{(1 - V)/(1 + V)(1 - 2V)} \qquad (6)$$

where V is the Poisson Ratio of the rock sample material.

To account for departures from elastic behavior of the rock and damping due to pore fluids a more refined analysis can be used. The damping coefficient $\epsilon$ can be determined from analysis of displacement amplitude vs. frequency data and from measurements of phase shift between driving signal and displacement. Viscoelastic constants which account for pore fluid behavior can be derived from this analysis and used to calculate velocity attenuation and reflection coefficient at interfaces. Results obtained in this way take account of the influence of pore fluids in the rock sample.

The frequency range of investigation depends on masses 13 and 14, on E for the rock material 10 and on sample dimensions. For a cylindrical rock sample 10 with E of $10^6$ psi, core diameter of 0.30 inches, wire length of 8 inches, and masses of 20 lbs. each, the resonant frequency f is about 93 hertz. Higher frequencies can be investigated by decreasing masses 13 and 14, decreasing rock sample 10 in length or increasing rock sample 10 in diameter. Lower frequencies can be obtained by making changes in the opposite sense.

Figure 2:
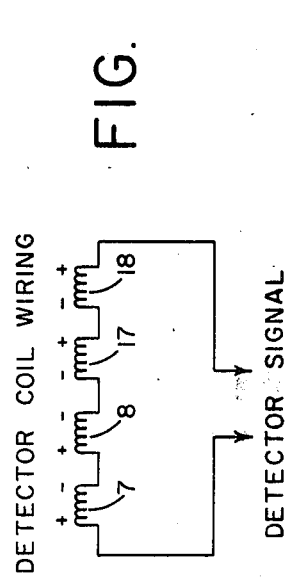
FIG. 2 illustrates a detection system for use in measuring displacements of the masses of the harmonic oscillator of FIG. 1.

Measurement of $f_m$ requires a method for measuring the displacements $X_1$ and $X_2$ of the masses 13 and 14, respectively, or their difference. One method for measuring the relative displacement $|X_1-X_2|$ is illustrated in FIG. 1. A pair of identical permanent magnets 5 and 6 are attached to the mass 13 and a pair of identical permanent magnets 11 and 12 are attached to the mass 14 with their axes lying in a plane perpendicular to the plane of the wire supports, 15 and 16. Identical coils 7, 8, 17 and 18 are positioned in the air gaps of each of the magnets 5, 6, 11 and 12 respectively. These coils are rigidly mounted on the oscillator frame through alignment brackets, 19. Motion of the masses produce an emf in the detector coils. By connecting the coils in series with appropriate polarity as shown in FIG. 2, the signals due to motion of the masses in oppositon add and give an emf proportional to $|X_1-X_2|$.

The geometry of the coil-magnet detectors used here is very effective in reducing noise due to wobble of the masses. Wobble, which produces lateral motion of the masses, does not induce significant emf in the coils. Wobble associated with motion of the masses in the same direction is highly damped and therefore not significant. Wobble associated with rotation of the masses about their wire supports produces flexure of the rock sample and is the dominant noise signal in the measurements. However, because of the coil-magnet arrangement this wobble produces signals of opposite polarity in the detector coils which tend to cancel thereby reducing the noise signal to a very low level. Any of a number of methods can be used to detect the emf signal produced in the detector coils of FIG. 2 by oscillation of the masses. A sensitive digital voltmeter could be used for this purpose. Amplifications of the coil signals by means for commercial amplifiers is helpful but not required. In accordance with the present invention, a quadrature detection method is used in place of a voltmeter since such method allows detection of very small oscillators, reduces noise and provides phase data as well. Quadrature detection systems, which are commercially available from Ithaco, Inc., Ithaca, N.Y. or from Princeton Applied Research, Princeton, N.J., are suitable for this purpose.

Figure 3:
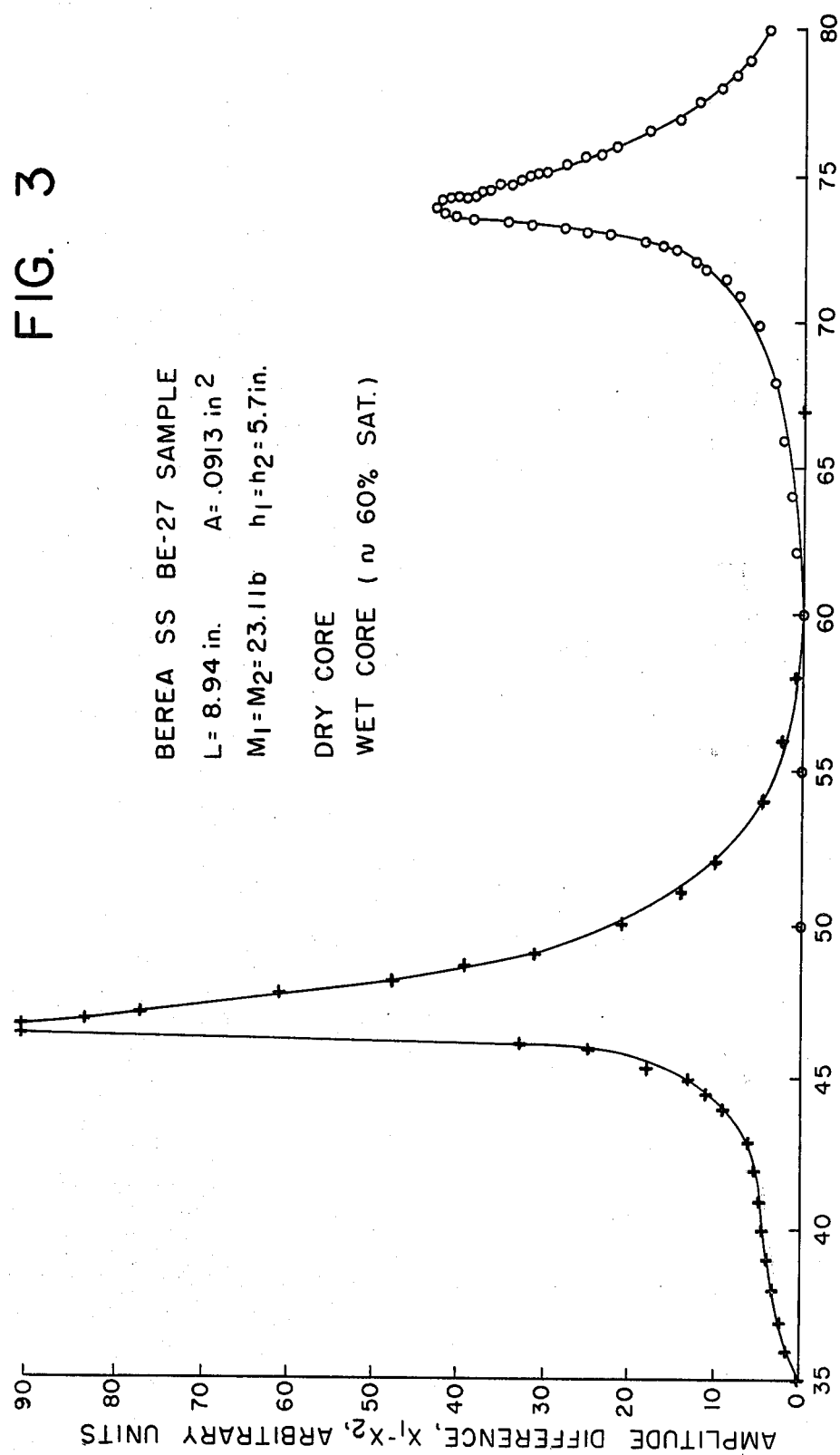
FIGS. 3 & 4 show resonance measurements carried out by the harmonic oscillator of FIG. 1.

Using a quadrature detector system, or any other means of detection, the resonant frequency $f_m$ can be determined by plotting the coil emf against frequency f of the driving current. FIG. 3 shows resonance measurements made for a Berea sandstone sample in the harmonic oscillator of FIG. 1. Dimensions of the cylindrical rock sample were a diameter of 0.341 inches and a length of 8.94 inches. Masses 13 and 14 were 23.1 lb each and the lengths of wires 15 and 16 were 5.7 inches. Results are shown for the sample in a dry state and in a wet state where saturation conditions were about 60% water and 40% gas. The dry state resonance frequency of 73.9 Hz. corresponds to a Young's modulus of $65\times10^6$ psi and V=4800 ft/sec. The wet state value resonance frequency of 46.5 hz. corresponds to a Young's modulus of $0.26\times10^6$ psi and V=3020 ft/sec.

Figure 4:
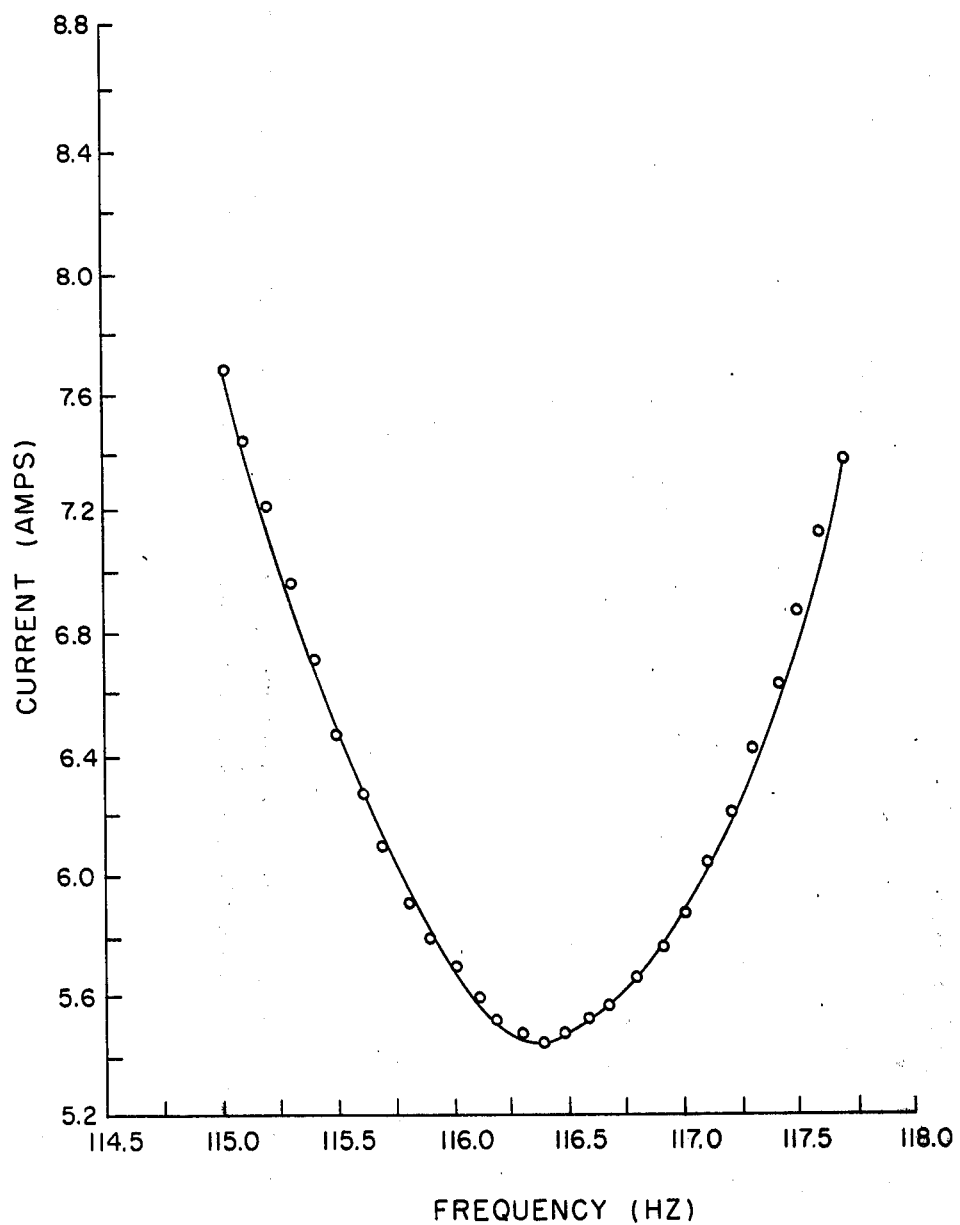

Most rock materials show significant non-linear resonance behavior. Near resonance the amplitude of oscillations changes with time and depends on how resonance is approached. The resonance peak itself does not fit the classical equations for a simple harmonic oscillator very well. These problems can be avoided by making the resonance measurements at constant amplitude. This can be done by means for adjusting the driving current (not shown) at each frequency to obtain a preselected amplitude $|X_1-X_2|$ such as 500 Angstroms. A plot of driving current vs. frequency then replaces the amplitude plot of FIG. 3. A typical measurement of this type is shown in FIG. 4. The resonance curve is inverted in this case with frequency corresponding to a minimum current rather than a maximum amplitude. However, the equations for a simple harmonic oscillator still apply to the driving current curve in a conventional way.

Constant amplitude measurements made in this way fit the classical harmonic oscillator equations very closely. Therefore the shape of the resonance peak can be used to measure damping of seismic frequency waves through the loss factor $Q_E = \frac{1}{2}E$. The $Q$ associated with longitudinal oscillations is called $Q_E$, the extensional loss factor, and is given by $$Q_E = \frac{f_m}{f_2 - f_1} \quad (7)$$

where $f_1$ and $f_2$ are the frequencies at which the driving current is $\sqrt{2}$ times the current at the resonant frequency $f_m$. If a quadrature detector or other system is used which provides phase data, $f_1$ and $f_2$ are the frequencies at which the phase angle $\phi$ between displacement signal and driving current is 135° and 225°, respectively, where $\phi$ is taken to be 180° at $f = f_m$.

Measurement of resonance data can be made in the harmonic oscillator of FIG. 1 for various pore fluid contents. In this way the role of pore fluids in altering wave velocity and attenuation and reflection coefficients at interfaces can be evaluated for various kinds of rocks. For this kind of analysis the rock sample is sealed in a plastic sleeve material which does not affect the mechanical properties of the rock. Commercially available, heat-shrinkable, plastic tubing, manufactured under the trade name, RNF shrink tubing, is suitable for this purpose. Various ratios of gas/water/oil saturations can be introduced into the core after it has been sealed by shrinking a jacket of this material around the sample.

Figure 5:
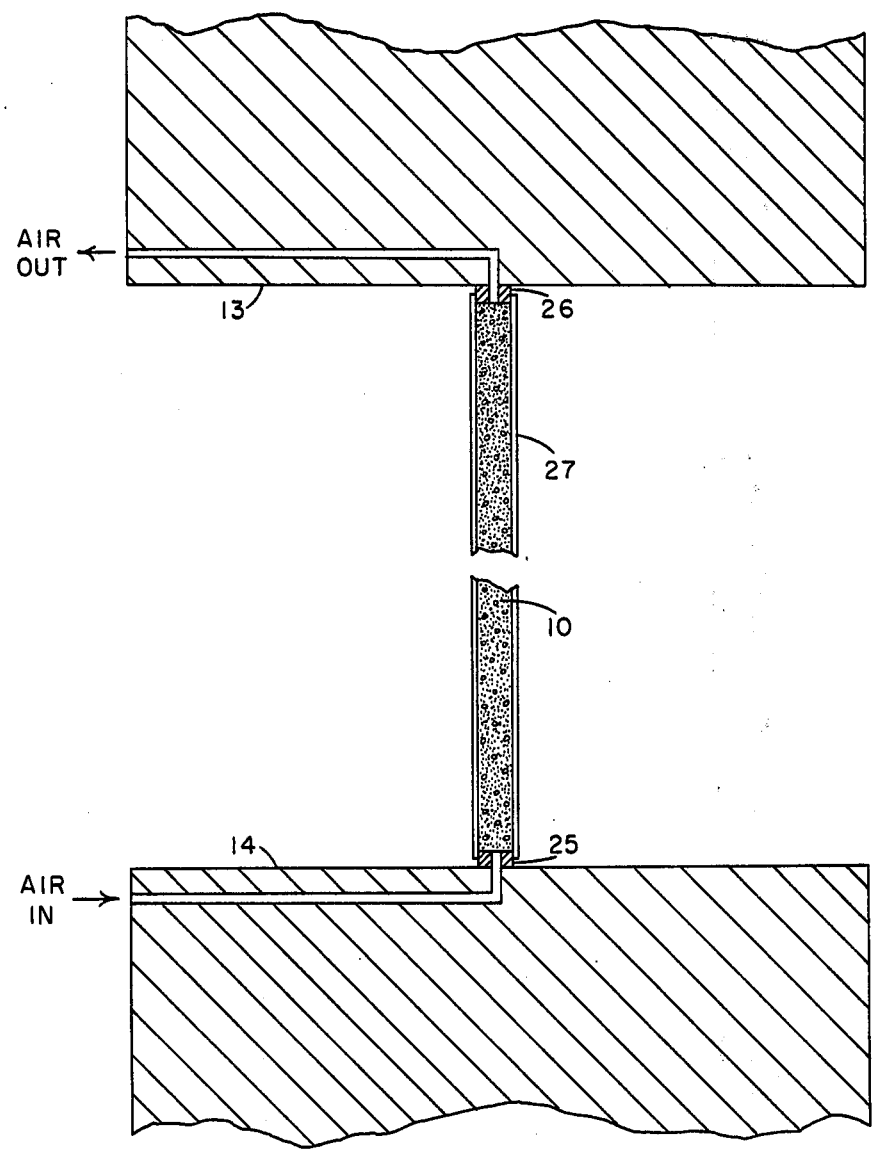
FIG. 5 shows the air flow path through the rock sample for use in measuring resonance data for various pore fluid contents.

As an example, a complete range of gas/water saturations can be obtained by the configuration of FIG. 5. The rock sample 10 is initially saturated in a vacuum system by conventional means to 100% salt water saturation. The sample is then sealed with heat shrinkable tubing 27 and is clamped by means of the end caps and steel clamping fixtures 26 and 27 between the masses 13 and 14. Epoxy beads are used to seal the edges of the shrink tubing jacket overlapping the end caps. Port holes are included in the end caps which communicate through steel capillary tubes with capillary holes in the support wires 15 and 16 in such a way that air can be blown through the core as shown in FIG. 5. Measurements are made at 100% initial water saturation. The air is blown through the core until the water saturation is reduced by a suitable increment and a new resonance measurement is made. This procedure is repeated until the entire range of water saturation is covered down to 0%. Water saturation may be determined at each step by means of electrical conductivity measurements across the rock sample or by removing the sample from the clamping fixtures and weighing. A calibration curve is obtained for the electrical conductivity measurement in a separate but identical rock sample which can be weighed after each incremental reduction in water saturation.

In the foregoing described embodiment of the invention, the harmonic oscillator of FIG. 1 has been described as a symmetric system with the masses 13 and 14 being driven in opposition by the means of the magnets 11 and 12 and driving coils 17 and 18. However, the system need not be symmetric to obtain useful results. Mass 13 can be different from mass 14 and one of the magnet-driving coil combinations can be removed. In such a non-symmetric system, the mass M in equations 1, 3 and 5 above may be replaced by the expression $$M = 2M_1 M_2 / (M_1 = M_2). \quad (8)$$

While various embodiments of the invention have been shown and described, additional modifications are within the spirit and scope of the invention. The appended claims are intended to cover all such modifications.

What is claimed is:

1. A harmonic oscillator for measuring dynamic elastic constants of rock materials at seismic frequency, comprising:
   (a) a pair of masses,
   (b) means for independently and vertically suspending each of said masses from a support position such that said masses can swing or vibrate in pendulum-like fashion,
   (c) a permanent magnet mounted on one of said masses,
   (d) a coil positioned in the air gap of said magnet,
   (e) means for connecting a sinusoidal seismic frequency to said coil for applying a driving force through said magnet to said mass,
   (f) means for horizontally supporting a rock material between said masses, the weight of said masses being large relative to the weight of said rock material to permit said rock material to vibrate at seismic frequencies, thereby forming a simple harmonic oscillator with said rock material acting as the spring element connecting said masses as they vibrate in pendulum-like fashion, and
   (g) means for measuring the relative displacements of said masses said relative displacements being a measure of the dynamic elastic constant of said rock material.

2. The mechanical oscillator of claim 1 wherein said pair of masses are the same weight.

3. The mechanical oscillator of claim 1 wherein said pair of masses are of dissimilar weight.

4. The mechanical oscillator of claim 1 further comprising:
   (a) a second permanent magnet mounted on the second of said masses,
   (b) a second coil positioned in the air gap of said second permanent magnet,
   (c) means for connecting said sinusoidal frequency to said second coil for applying a driving force through said second magnet to the second of said means.

5. The mechanical oscillator of claim 4 wherein said masses are driven in opposition with each other.

6. The mechanical oscillator of claim 1 wherein said displacement measuring means comprises:
   (a) a pair of coil-magnet detectors,
   (b) means for mounting said coil-magnet detectors to said one of said masses in a location to reduce noise signals,
   (c) means for measuring the emf generated in said detector coils as said masses oscillate, said emf being a measure of the dynamic Young's modulus and extensional loss factor of said rock material at seismic frequency.

7. The mechanical oscillator of claim 1 further comprising means for adjusting the driving current of said sinusoidal seismic frequency to said coil for each frequency of oscillation so as to maintain a constant amplitude oscillation at or near seismic amplitude levels.

8. The mechanical oscillator of claim 7 furrher comprising means for determining the extensional loss factor, $Q_E$, associated with longitudinal oscillations through the following relationship:

$$Q_E = f_m/f_2 - f_1,$$

where, $f_m$ = resonant frequency
$f_1$ & $f_2$ = frequencies at which the coil-magnet driving current to the pair of masses is 2 times the current at resonant frequency.

* * * * *